US012758500B2

(12) United States Patent
Hung

(10) Patent No.: US 12,758,500 B2
(45) Date of Patent: Oct. 13, 2026

(54) PHARMACEUTICAL COMPOSITION FOR IMPROVING RESPIRATORY DAMAGE AND USE FOR MANUFACTURING PHARMACEUTICAL COMPOSITION FOR IMPROVING RESPIRATORY DAMAGE

(71) Applicant: Ming-Chien Hung, Taipei (TW)

(72) Inventor: Ming-Chien Hung, Taipei (TW)

( * ) Notice: Subject to any disclaimer, the term of this patent is extended or adjusted under 35 U.S.C. 154(b) by 286 days.

(21) Appl. No.: 18/591,896

(22) Filed: Feb. 29, 2024

(65) Prior Publication Data

US 2024/0252439 A1 Aug. 1, 2024

Related U.S. Application Data

(63) Continuation-in-part of application No. 17/335,124, filed on Jun. 1, 2021.

(51) Int. Cl.

| | |
|---|---|
| ***A61K 45/06*** | (2006.01) |
| ***A61K 9/00*** | (2006.01) |
| ***A61K 9/16*** | (2006.01) |
| ***A61P 11/00*** | (2006.01) |

(52) U.S. Cl.

CPC .......... *A61K 9/1611* (2013.01); *A61K 9/0073* (2013.01); *A61K 45/06* (2013.01); *A61P 11/00* (2018.01)

(58) Field of Classification Search

CPC .... A61K 9/1611; A61K 9/0073; A61K 45/06; A61K 9/0075; A61K 33/44; A61K 47/02; A61P 11/00

See application file for complete search history.

(56) References Cited

U.S. PATENT DOCUMENTS

| | | | | |
|---|---|---|---|---|
| 5,275,154 A * | 1/1994 | Von Blucher | A62B 23/02 128/205.27 |
| 9,999,598 B1 * | 6/2018 | Ko | A61K 33/38 |
| 2001/0001038 A1 * | 5/2001 | Matianich | A61K 49/006 424/9.1 |
| 2009/0297499 A1 * | 12/2009 | Foxwell | A61K 31/00 424/125 |
| 2014/0109899 A1 * | 4/2014 | Boucher | A61M 11/003 128/200.14 |

FOREIGN PATENT DOCUMENTS

| | | | |
|---|---|---|---|
| GB | 2486713 A * | 6/2012 | A61K 31/505 |
| WO | WO-2009067067 A1 * | 5/2009 | A61P 11/06 |

OTHER PUBLICATIONS

Jelavic et al. Peer Community Journal, vol. 2 (2022), article e80: 17 pages) (Year: 2022).*

PubChem Activated Charcoal ([online] retrieved on Feb. 4, 2026 from: https://pubchem.ncbi.nlm.nih.gov/compound/Activated-Charcoal; 3 pages). (Year: 2026).*

* cited by examiner

*Primary Examiner* — Ernst V Arnold

(74) *Attorney, Agent, or Firm* — Sinorica International Patent & Trademark

(57) ABSTRACT

The present invention provides a pharmaceutical composition for improving respiratory damage. The pharmaceutical composition includes an adsorbent medicament and a water-containing carrier, wherein said adsorbent medicament comprises a carbon material, a molecular sieve or a positively and negatively charged compound. The present invention also provides use for manufacturing pharmaceutical composition for improving respiratory damage.

7 Claims, 8 Drawing Sheets

PHARMACEUTICAL COMPOSITION FOR IMPROVING RESPIRATORY DAMAGE AND USE FOR MANUFACTURING PHARMACEUTICAL COMPOSITION FOR IMPROVING RESPIRATORY DAMAGE

CROSS REFERENCE OF RELATED APPLICATION

This is a Continuation-in-Part (CIP) application with application Ser. No. 17/335,124, filed on Jun. 1, 2021.

BACKGROUND OF THE PRESENT INVENTION

Field of Invention

The present invention relates to a pharmaceutical composition for improving respiratory damage, more particularly to a pharmaceutical composition for improving respiratory damage comprising an adsorbent medicament, and for manufacturing the pharmaceutical composition for improving respiratory damage.

Description of Related Arts

When pathogens, bacteria, poisons, fire smoke or foreign substances invade a lung, it would cause inflammation and activate immune cells, such as white blood cells, macrophages, and natural killer cells. Moderate inflammation is beneficial for the immune cells to eliminate pathogens from the body, but the inflammation might be intensified by some substances, for example viruses (such as COVID-19, SARS-CoV-2, MERS-COV, influenza viruses (including type A, type B, type C, and type D; examples of influenza A viruses: H1N1, H5N1, H7N9; the foregoing influenza viruses not only infecting humans, but also able to cross-transmit between species like poultry, dogs, pigs, and cows), AIDS viruses, avian influenza viruses, Ebola viruses, hantaviruses, anthrax viruses, Lassa viruses, West Nile viruses, Zika viruses, respiratory syncytial viruses (RSV), Dengue fever viruses, or other viruses that cause viral hemorrhagic fevers); bacteria (common examples: *Streptococcus pneumoniae, Haemophilus influenzae*, and *Mycobacterium tuberculosis*); fungi (common examples: black fungus and white fungus; often appearing in patients with diabetes, transplants, blood-related malignancies, or long-term steroid treatment); poisons, such as phosgene and chlorine. For instance, exposure to high concentrations of phosgene may cause pulmonary edema and difficulty breathing. Moreover, exposure to even higher concentrations of phosgene may cause severe lung injury, possibly leading to death. Radiological examinations, such as chest X-rays, may be the fastest way to confirm whether the lungs are damaged by poisons.

If the lung is invaded by the above-mentioned substances, it is easy to cause hyperactive inflammation, inducing cells massively releasing cytokines, wherein proinflammatory cytokines and chemokines are the main cause of cytokine storm, which further triggers more immune cells gathering around infected lung epithelial cells, continually producing even more proinflammatory cytokines and chemokines, thus causing pulmonary swelling, injury, infiltration, fibrosis, and failure. It may even result in shock and high mortality rate.

The current treatment plan targeting pathogen replication process prior to the development of cytokine storm is medicament therapies, such as antibiotics, antiviral medicine, and steroids. For example, antiviral medicine is used to inhibit virus replication. Once entering cytokine storm, currently on treatment, there is no powerful and effective medicine against cytokine storm. Supportive therapy is the only option to endure patients through the critical stage of illness. For instance, steroids previously have been used to treat cytokine storm induced by SARS to curb the immune response so as to reduce inflammation. Yet, suppressing a body's immune response often causes the disease rapidly deteriorated and out of controlled, increasing in mortality rate instead. Besides, steroid treatment is not recommended in certain clinical guidelines for novel viruses (such as COVID-19). In addition to lowering the immunity of a patient, steroid treatment may mask a fever response in his immune system, and, as a result, the treatment opportunity may be missed. At the same time, more people may be infected, leading to an epidemic outbreak. The current main therapy for COVID-19 cytokine storm involves supportive treatment via supplying sufficient oxygen to infected patients, tapping the patients' back to loosen sputum, and monitoring blood pressure, and the like, to help the patients survive the two-week acute period. Apart from that, the patients can only rely on their own immune systems to produce antibodies and regain health.

However, none of the above-mentioned medicament treatments or supportive therapies can be employed to control, relieve, or treat inflamed areas in lungs. Conventional technology used to remove harmful substances from the lung at the foregoing stage is to exam the lung with a bronchoscope or a nasogastric tube, and then irrigate the lung with normal saline to wash away and eliminate these harmful substances, thereby restoring lung gas exchange capacity. However, toxic substances (such as endotoxins), bacteria, viruses, proinflammatory cytokines, chemokines, or cytokines, and the like, which are adhered to the lungs, cannot be easily washed out by normal saline. Therefore, it is more difficult to lower or restore white blood cell counts, inflammation, bleeding volume, white blood cell indices, etc. back to their normal values.

SUMMARY OF THE PRESENT INVENTION

In order to solve the aforementioned shortcomings, the present invention provides a pharmaceutical composition for improving respiratory damage.

According to one object of the present invention, the present invention provides a pharmaceutical composition for improving respiratory damage. The pharmaceutical composition comprises an adsorbent medicament and a water-containing carrier, wherein said adsorbent medicament comprises a carbon material, a molecular sieve or a positively and negatively charged compound.

In accordance with another object of the present invention, the present invention provides an application for manufacturing pharmaceutical composition for improving respiratory damage, wherein said pharmaceutical composition comprises an adsorbent medicament and a water-containing carrier, wherein said adsorbent medicament comprises a carbon material, a molecular sieve or a positively-/negatively-charged compound.

The pharmaceutical composition according to the present invention has a certain efficacy against pneumonia, regardless of the disease progression, and achieves the effect of improving respiratory damage.

DETAILED DESCRIPTION OF THE PREFERRED EMBODIMENT

Figure 1:
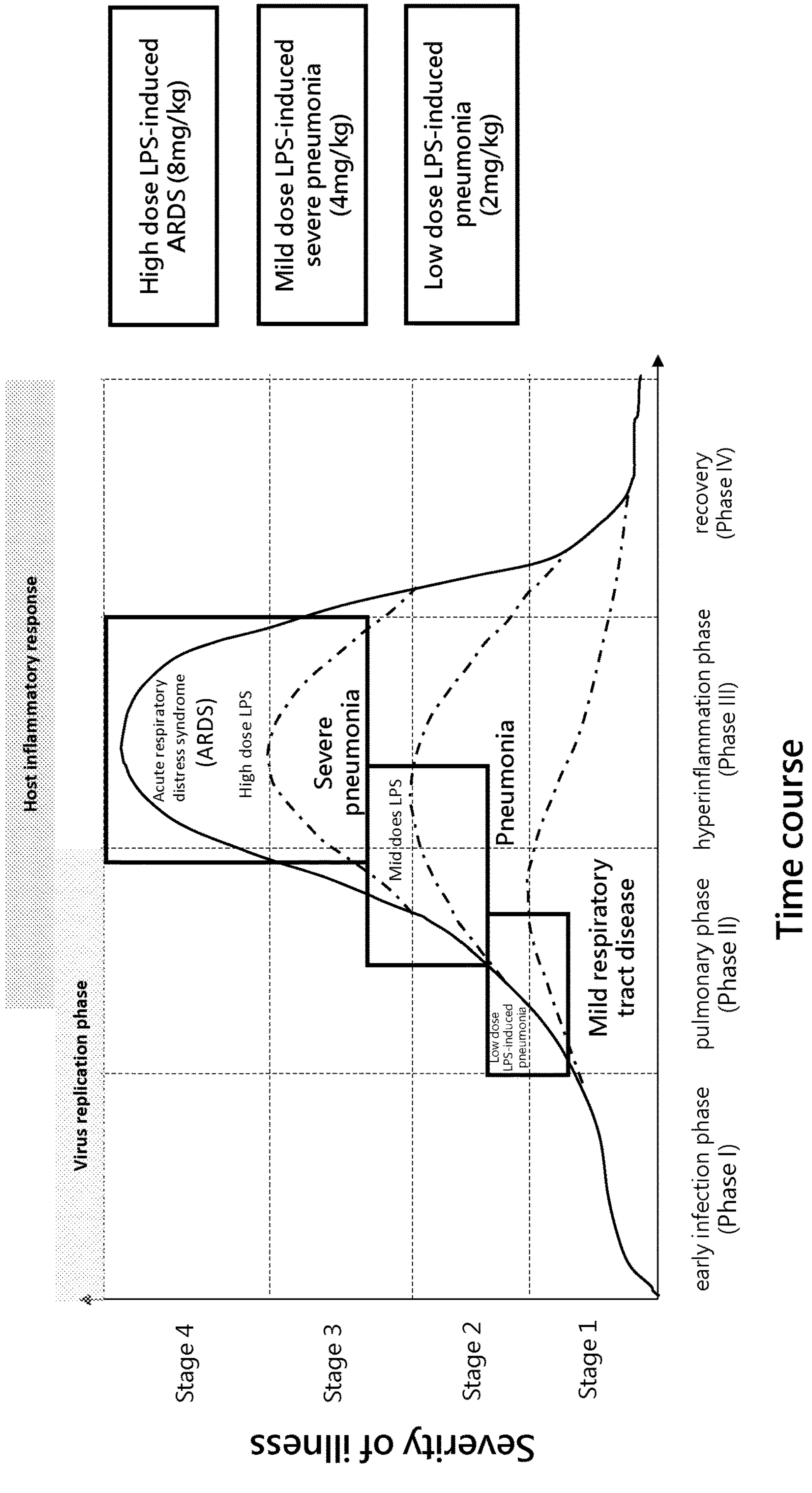
FIG. 1 is a schematic diagram of the present invention using different concentrations of lipopolysaccharides to induce lung injuries mimicking different progressions of the novel coronavirus pneumonia.

In order for a person having ordinary skill in the art to which the present invention pertains to be able to further understand the present invention, the following description will list the preferred embodiments of the present invention, in conjunction with the drawings, explaining in detail the contents of the present invention and the effects to be achieved.

The present invention provides a pharmaceutical composition for improving respiratory system. An active ingredient of said pharmaceutical composition comprises an adsorbent medicament. In one embodiment of the present invention, the pharmaceutical composition may further comprise a water-containing carrier, an adjuvant, an excipient or a propellant. “Respiratory” according to the present invention refers to the respiratory tract (including the nasal cavity, pharynx, larynx, trachea, and bronchi) and the lungs. The pharmaceutical composition provided by the present invention may be used for treating damages caused by common respiratory diseases. The concept is that it contains an adsorbent medicament, which may adsorb proinflammatory cytokines, chemokines, cytokines, bacteria, viruses, fungus, or toxic substances (from e.g., fire, nuclear, biological, and chemical sources) in the respiratory system. It may treat or relieve inflammation or infection in the upper respiratory tract, for example, inflammation or infection associated with lungs and car nose and throat (ENT) system, such as oropharynx inflammation. Additionally, it may treat or relieve inflammation or infection in the lower respiratory tract, for example pneumonia, respiratory infection, infection or inflammation caused by lung expansion apparatuses, ventilator associated pneumonia (VAP), mild respiratory disease, acute tonsillitis, acute laryngitis, bronchitis, pleurisy, bronchiectasis, cribriform inflammation, lung abscess, asthma, adult viral pneumonia, adult bacterial pneumonia, extrinsic allergic alveolitis, hypersensitivity pneumonitis, hemorrhagic pneumonia, tuberculosis pneumonia, farmer’s lung, legionnaire’s disease, *Mycobacterium avium*’s disease, *mycoplasma* pneumonia, emphysema, aspiration pneumonia, hydrocele pulmonary edema, lung injury, acute pneumonia, chronic pneumonia, severe pneumonia, acute respiratory distress syndrome (ARDS), pulmonary fibrosis or chronic pulmonary obstruction (COPD) or other indications where the airway can be improved and treated by cleaning the lungs, wherein the symptoms are associated with the above said diseases, such as difficulty breathing, intra alveolar edema, pulmonary inflammation, pulmonary hemorrhage, pulmonary infiltrate or pulmonary cytokine storm, and further ameliorate injuries in respiratory system. The pharmaceutical composition for improving respiratory damage of the present invention may mitigate the degrees of pulmonary edema, inflammation, hemorrhage, or cytokine storm, such that the immune response can be controlled at a non-fatal level without affecting the immune system’s ability to clear pathogens or foreign substances, and therefore the patient’s immunity can be preserved and the mortality rate can be effectively reduced.

In one embodiment, “patient” refers to an animal that can be effectively treated by the combination of the active agents described herein. In one embodiment, the patient is human.

In one embodiment, the adsorbent medicament is any one or a combination of a carbon material, a molecular sieve, a positively-/negatively-charged compound.

In one embodiment, the carbon material may be selected from, but is not limited to, activated carbon, activated carbon fiber, carbon fiber, carbon ball, activated carbon ball, columnar activated carbon, activated carbon powder, carbon powder, Fullerene (C60), cellulose carbon, bamboo carbon, soot, carbon aerogel, graphite, expanded graphite, carbon nanotube, carbon nanosphere, coke ball, or carbon black, or a combination thereof. In one embodiment, a carbon material has a specific surface area (SSA) (calculated using the BET method) of 300 to 3000 $m^2/g$; preferably of 600 to 2000 $m^2/g$; more preferably of 900 to 1850 $m^2/g$. In one embodiment, said carbon material has a mean particle diameter of 0.1 to 500 μm; preferably of 0.5 to 50 μm. In one embodiment, said carbon material has a volume in pores of 0.1 to 3.0 ml/g, preferably 0.1 to 1.0 ml/g. In one embodiment, the carbon material has a micropore diameter of 1 to 500 nm, preferably of 2 to 200 nm. In one preferred embodiment, the pharmaceutical composition further comprises a water-containing carrier and the carbon material in a water-containing carrier has a concentration of 0.001 to 1 wt %.

In one embodiment, the molecular sieve may be a variety of materials with uniform microporous structures. Its structure may be type A molecular sieve (including 3A molecular sieve, 4A molecular sieve, 5A molecular sieve), type X molecular sieve (13X molecular sieve, 10X molecular sieve). The material may be adjusted as the situations require, and may include aluminosilicate, coal, and other bio-acceptable materials, but is not limited thereto.

In one embodiment, the positively and negatively charged compounds may be molecular polymers (polyelectrolytes), ion-exchange resin, ionic surfactant, and the like. The above-said positively and negatively charged compounds, through acidic or basic functional groups, dissociates hydrogen ions ($H^+$) or hydroxide ions ($OH^-$) in the solution, to allow the compound carrying negatively charged groups (such as $SO_3^-$, or R—COO⁻) to bind other cations through adsorption in the solution, or carrying positively charged groups (such as R—$NR_3^+$) to bind other anions through adsorption in the solution. For example, pathogens or bacteria carry positive or negative charges (e.g., viral envelop amino acids carrying negative charges). Therefore, the adsorbent medicament including the positively and negatively charged compound may adsorb viruses so as to prevent spreading viruses.

In one embodiment, the pharmaceutical composition can be implanted by individually using the adsorbent medicament, or further comprises a water-containing carrier. In one embodiment, the water-containing carrier of the pharmaceutical composition enables the adsorbent medicament to enter respiratory tract in a suspended solid form, allowing said pharmaceutical composition to be prepared as a spray, an inhalant, or a liquid suspension, but it is not limited thereto. In one embodiment, the water-containing carrier may be any physiologically compatible buffer solution for the respiratory system, such as normal saline, buffers, isotonic saline solution or a combination thereof. In one embodiment, the pharmaceutical composition has the adsorbent medicament carried by further containing a water-containing carrier, which is normal saline.

In one embodiment, the adjuvant of said pharmaceutical composition includes (but not limited to) (a) carbohydrates, for example, monosaccharides, such as fructose, galactose, glucose, D-mannose, sorbose and the like; disaccharides, such as sucrose, lactose, trehalose, cellobiose and the like; cyclodextrin, such as 2-hydroxypropyl-ß-cyclodextrin; and polysaccharides, such as raffinose, maltodextrin, polydextrose, starch, chitin, polyglucosamine, inulin and the like; (b) amino acids, for example, alanine, glycine, arginine, aspartic acid, glutamine, cysteine, lysine, leucine, isoleucine, valine and the like; (c) metals as well as organic salts prepared from organic acids and bases, for example, titanium, zinc, copper, silver, platinum, or gold, sodium citrate, sodium ascorbate, magnesium gluconate, sodium gluconate, tromethamine hydrochloride and the like; (d) peptides and proteins, such as VEGF polypeptide, PDGF polypeptide, aspartame, tri-leucine, human serum albumin, gelatin, gelatin and the like; (e) alditol, such as mannitol, xylitol, and the like; (f) synthetic or natural polymers or a combination thereof, such as polylactic acid, polylactic-glycolic acid, cyclodextrin, polyacrylate, methylcellulose, carboxymethylcellulose, polyvinyl alcohol, polyanhydride, poly-lactam, polyvinylpyrrolidone, hyaluronic acid, polyethylene glycol; and (g) surfactants, including fluorinated and non-fluorinated compounds, such as saturated and unsaturated lipids, non-ionic detergents, non-ionic block copolymers, ionic surfactants, and a combination thereof; and (h) nutrients, including water-soluble vitamins or fat-soluble vitamins; and (i) antioxidant medicament: ascorbic acid (vitamin C), glutathione, lipoic acid, coenzyme Q10, ubiquinone (coenzyme Q), α-tocopherol (vitamin E), carotene, or a combination thereof; and (j) corticosteroids, including dexamethasone, beclomethasone, budesonide, ciclesonide, flunisolide, fluticasone, methyldehydrocortisol, mometasone, preisone and triamcinolone, including any pharmaceutically acceptable salts, esters, isomers or solvates thereof. When the composition includes corticosteroids as an active agent, in one preferred embodiment, optionally, it may be dexamethasone.

In one embodiment of the present invention, the pharmaceutical composition further comprises a salts, where the salts can be pure salt, sea salt, or sodium bicarbonate. The pharmaceutical composition is in dry powder form, packaged in bags, glass bottles, or syringes for convenient storage and transportation. It allows users to add a solvent such as water or distilled water to prepare a hypertonic saline solution containing the adsorbent medicament. In this way, the adsorbent medicament, including the positively and negatively charged compound, may adsorb viruses, preventing the spread of viruses.

In one embodiment, the excipient of said pharmaceutical composition includes, but not limited to, one or more of tri-leucine, sodium citrate, sodium phosphate, ascorbic acid, inulin, cyclodextrin, polyvinylpyrrolidone, mannitol, sucrose, trehalose, lactose, sodium chloride, glucose, urea, starch, calcium carbonate, kaolin, crystalline cellulose, silicic acid, proline, water, ethanol, propanol, corn starch, simple syrup, glucose solution, starch solution, gelatin solution, shellac, potassium phosphate, methyl cellulose, sodium carboxymethyl cellulose, ethyl cellulose, hydroxyethyl cellulose, hydroxypropyl methylcellulose, low-substituted hydroxypropyl cellulose, microcrystalline cellulose (MCC), aldehyde cellulose, or hydroxypropyl methylcellulose phthalate, collagen, hyaluronic acid, gelatin or gel, quaternary ammonium salt, sodium lauryl sulfate, and surfactant.

In one embodiment, the propellant of said pharmaceutical composition refers to a gas suitable for liquefaction under pressure at room temperature, and, when inhaled or used topically, considered as safe and toxicologically non-toxic. In addition, the selected propellant together with adsorbent medicament do not have relative reactivity. The propellant includes (but not limited to) perfluorinated compounds (PFC), hydrofluoroalkanes (HFA), fluoroheptane, fluorocycloheptane, fluoromethylcycloheptane, fluorohexane, fluorocyclohexane, fluoropentane, fluorocyclopentane, fluorine methylcyclopentane, fluorodimethylcyclopentane, fluoromethylcyclobutane, fluorodimethylcyclobutane, fluorotrimethylcyclobutane, fluorobutane, fluorocyclobutane, fluoropropane, fluorine ether, fluoropolyether and fluorotriethylamine.

In one embodiment of the present invention, said pharmaceutical composition further comprises a medicine. Said medicine is, for example, antibacterial medicine; antiviral medicine (varying depending on virus types, including, but not limited to, remdesivir, camostat mesylate, lopinavir, ritonavir, favipiravir, umifenovir, adenosine nucleotide analogues, protease inhibitor, RNA polymerase inhibitor, fusion inhibitor, cytokine, entecavir, imipenem, interferon); benzene-ring medicine; anticoagulant medicine (such as heparin, coumarin, clopidogrel, ethylenesalicylic acid, warfarin, rivaroxaban, apixaban, edoxaban, or enoxaparin sodium); thrombolytic medicine (such as tissue-type plasminogen activator (tPA), recombinant tissue plasminogen activator (rt-PA), thrombomodulin (TM), thrombolytic enzyme, or fondaparinux); alpha-blockers (such as α-adrenoceptor blockers, terazosin (Hytrin tablets), doxazosin (Doxaben tablets), tamsulosin (Harnalidge orally disintegrating tablets) or silodosin (Urief capsules)); 5α-Reductase inhibitors (such as finasteride (Proscar tablets) or dutasteride (Avodart soft capsules)); nasal decongestants; antitussives; expectorants; mucolytics; bronchodilators (such as beta2-agonists or anticholinergic medicine); antibiotics (such as aminopenicillins, carboxypenicillins, sulfonamides and trimethoprim-sulfamethoxazole (such as TMP-SMX), β-lactam antibiotics, unique β-lactam antibiotics (such as monobactams or carbapenems), non-β-lactam antibiotics (such as macrolide or tetracycline), cephalosporins, macrolides, fluoroquinolones (FQ), vancomycin, rifapentine, chloramphenicol, or tigecycline); antifungal medicines (such as amphotericin B, imidazoles, triazoles, griscofulvin, nucleoside analogue antifungals, polyene antifungals, triazole antifungals (such as voriconazole, itraconazole, or posaconazole), echinocandin antifungals, voriconazole antifungals, azole antifungals, isavuconazole, flucytosine, or fluconazole); anti-asthmatic drugs, anti-inflammatory drugs (such as anti-leukotriene agents, steroids, or non-steroid anti-inflammatory drugs (NSAIDs)); antioxidants (for anti-inflammation and anti-free radicals, such as melatonin or anthocyanins); Chinese medicine extracts (such as maxing shigan decoction extracts (roasted ephedra, cinnamon twig, bupleurum root, fresh ginger, wrinkled giant hyssop, poria, polyporus, alisma, pinellia, asarum, tangerine peel, white atractylodes rhizome, tatarian aster, coltsfoot flower, blackberry lily, skullcap root, gypsum, unripe orange fruit, almond, yam, roasted licorice); isoflavone derivatives; flavonoids; volatile oil from *Houttuynia cordata*; quercetin; quercetin; decanoyl acetaldehyde; lauric aldehyde; 1-pinene; linlool; camphene; myrcene; limonene; bornyl acetate; caryophellene; afzelin; hyperin; rutin; quercitrin; flowers and fruit clusters with isoquercitrin; honeysuckle; triterpene saponin; luteolin; lonicerin; hyperoside; dandelion; rosmarinic acid; oleanolic acid; ursolic acid; rutin; prunella spike; pseudo-dandelion sterol palmitic acid; chlorogenic acid; iso-chlorogenic acid; caffeic acid; alkaloids; fritillarine; linarin; phenylpropanoid glycoside; iridoids; isatis root injection (4(H quinazolinone, 3 red carboxylphenyl)-1(H) quinazolinone, benzoic acid, syringic acid, anthranilic acid, salicylic acid, etc.); antibodies (such as Tocilizumab, Sarilumab and Eculizumab, Kevzara, Actemra); vaccines (able to combine with the adsorbent medicament of the present invention, such as mRNA vaccines, protein vaccines, adenovirus vaccines, attenuated vaccines, molecular vaccines or nano-vaccines); or even the plasma from a cured person; or a combination thereof, but it is not limited thereto.

In one embodiment of the present invention, a coating may further be formed on the adsorbent medicament to adsorb inflammatory substances or harmful substances or to increase the connections with other adjuvants, excipients, propellants and water-containing carriers. In one embodiment, the surface of the adsorbent medicament may be altered/modified by using oxygen plasma, soaking acid, electroplating, coating, etc., so that the surface is altered/modified to form a coating on the surface. In another embodiment, the coating may include oxygen functional groups (attached to the surface of the carbon material by using plasma treatment to adsorb viruses or endotoxins in molecular chain structure), hydroxyl functional groups (attached to the surface of the carbon material by using soaking acid treatment to adsorb viruses), hydroxyl, carboxylic acid, aldehyde groups, carbonic acid, metal ions (attached to the surface of the carbon material by using high temperature or electroplating treatment to inactivate viral envelop, to inhibit viral activity, or to kill viruses; e.g., silver, platinum, palladium, gold, zinc, or copper; preferably, silver ions), magnetic materials (used to strengthen the adsorption capacity of the carbon material and reduce the residues from harmful substances; preferably, iron ions), cation compounds (such as compounds containing calcium, magnesium, potassium, sodium, like calcium carbonate or calcium phosphate), anion compounds (such as sodium triiodide), or halogen ions (such as fluorine, chlorine, bromine, and iodine), or a combination thereof.

In another embodiment, metal ions may further be bound to the surface of said adsorbent medicament. Said metal ions may be silver, platinum, palladium, gold, zinc, or copper; preferably, activated carbon fiber powders containing silver ions; less preferably, carbon fiber powders containing silver ions. In addition, said carbon material containing silver ions also has the effect of adsorbing viruses, inactivating viral envelop, and relieving cytokine storm damage, etc., so as to reduce the risk of patients' death. Furthermore, in another preferred embodiment, they may be activated carbon fiber powders containing zinc ions, or carbon fiber powder containing zinc ions. In another embodiment of the present invention, said adsorbent medicament may also mix with a variety of nano drug delivery systems or carriers, for example, liposome, nano-pathogens, nano-bacteria or molecular robot. Said nano drug delivery system may also combine with various aspects of coatings as described above, for example, nanoballs, metal ions, cation drugs, anion drugs, and magnetic materials, to increase overall stability, or to increase its function.

The harmful substances adsorbed by the composition of the present invention may be: toxic substances (such as endotoxins), bacteria, viruses, proinflammatory cytokines, chemokines, or cytokines. The present invention may further comprise use of a pharmaceutical composition for improving respiratory damage. Said pharmaceutical composition may be formulated as a spray or an inhalant or a liquid suspension. When in use, said pharmaceutical composition may be inhaled via a nebulizer or as dry powders (that is, using only adsorbent medicament and without using water-containing carrier), or perfused into the patient's nasal cavity, throat, and specific or unspecific cavities of the lungs (such as pulmonary bronchi or secondary bronchi/bronchioles) through an equipment (such as thoracoscope, endoscope, bronchoscope, infusion tube, infusion bag, infusion pump, or syringe.) Also, it may further be paired with single lobe lavage, whole-lung lavage, or bronchoalveolar lavage for treatment, using normal saline to remove said pharmaceutical composition as well as harmful substances adsorbed therefrom.

The present invention provides use of a pharmaceutical composition for improving respiratory damage. One aspect of said use for the pharmaceutical composition is in a dosage form of a spray or an inhalant using a dosage of 10 ml to 100 ml through a gas administration system, such as a nebulizer, for approximately 20 minutes, or using 0.1 mg to 10 mg through a dry powder inhaler, for approximately 20 minutes. Said pharmaceutical composition is delivered to pulmonary bronchi or secondary bronchi/bronchioles and said dry powder inhaler means using only adsorbent medicament without using water-containing carrier. Another aspect of said use for the pharmaceutical composition is in the form of a liquid droplet injection, administered in a dosage of 10 ml to 100 ml via instillation to each lobe of the lungs. Then, the patient produces sputum to remove said pharmaceutical composition out of the lungs to complete the treatment course. If the physician assesses that the patient is unable to cough up sputum through the cilia movement, said pharmaceutical composition may further be paired with whole-lung lavage or bronchoalveolar lavage for treatment, using normal saline to remove said pharmaceutical composition as well as harmful substances adsorbed therefrom, so as to reduce subsequent residual risk.

The preparation method and relevant experiments of the present invention are illustrated in the following description to demonstrate the effects of the present invention.

Method for Preparing the Pharmaceutical Composition of the Present Invention

The carbon material in accordance with the present invention weighed 8 mg was added and well mixed to 50 ml of 0.9% normal saline. The carbon material is activated carbon powders without modification on surface. It has a specific surface area of 1248.8 $m^2/g$, a mean particle diameter of 12.08 μm, a median particle size distribution (d50) of 9.453 μm, and a volume in pores of 0.4285 ml/g.

Experimental Module

Referring to FIG. 1, a schematic diagram shows the present invention using different concentrations of lipopolysaccharides (LPS) to induce lung injuries mimicking different progressions of the novel coronavirus pneumonia in rats. The present invention uses lipopolysaccharides to induce ARDS as a pathological model to test the prophylactic use of compounds and therapy for ARDS in patients with the novel coronavirus. A lipopolysaccharide, a type of carbohydrates, can be purified from cell walls of Gram-negative bacteria. When delivered to the lungs of rodents via aerosol, it would induce Th1 immune responses, resulting in inflammatory cells (mainly neutrophils) to influx into the respiratory tract as well as resulting in a substantial increase of cytokines in lungs, thus causing varying degrees of ARDS. The present invention uses different concentrations of lipopolysaccharides to induce lung injuries mimicking the different progressions of the novel coronavirus pneumonia. As shown in FIG. 1, the time course of the disease represented on the horizontal axis includes early infection (phase I), pulmonary damage phase (phase II), cytokine storm (hyperinflammation) phase (phase III), and recovery phase (phase IV). Among them, when the pulmonary damage phase (phase II) progresses halfway, the inflammatory response in lungs could be observed, and reach the peak in the cytokine storm phase (phase III).

Normal blood oxygen saturation values in humans are above 95%. However, a COVID-19 patient has often developed “silent hypoxia”, a condition causing low blood oxygen levels in the patient’s body without trouble breathing. Therefore, the patient might delay in seeking medical care, which might impact the patient’s condition, more likely causing sudden death. It is mainly because the patient would develop severe pneumonia when the time course moves to pulmonary damage phase (phase II). According to the classifications of clinical manifestation associated with SARS-CoV-2 infection from WHO, the clinical symptoms of severe pneumonia are as following: fever or respiratory tract infection, plus one of the following: respiratory rate >30 breaths/min; severe respiratory distress; blood oxygen saturation ($SpO_2$)≤94% on room air. During cytokine storm stage (phase III), the patients might develop acute respiratory distress syndrome (ARDS). According to the classifications of clinical manifestation associated with SARS-CoV-2 infection from WHO, the clinical observations associated with acute respiratory distress syndrome (ARDS) patients are as followings: (1) chest imaging (X-Ray, CT scan, lung ultrasound, etc.) finds bilateral opacities, not fully explained by pleural effusion, lobar collapse, or nodules; (2) origin of edema: respiratory failure not fully explained by cardiac failure or fluid overload. Need objective assessment to exclude hydrostatic pulmonary edema; (3) oxygenation (adults): “mild ARDS”: 200 mmHg$<PaO_2/FiO_2\leq$300 mmHg (with PEEP or CPAP≥5 cm $H_2O$, or non-ventilated); “mild ARDS”: 100 mmHg$<PaO_2/FiO_2\leq$200 mmHg (with PEEP≥5 cm $H_2O$, or non-ventilated); “severe ARDS”: $PaO_2/FiO_2\leq$100 mmHg (with PEEP≥5 cm $H_2O$, or non-ventilated). When $PaO_2$ is not available, $SpO_2/FiO_2\leq$315 mmHg suggests ARDS (including in non-ventilated patients).

Severity of illness on the vertical axis can be divided into four categories: mild respiratory tract illness (stage 1), pneumonia (stage 2), severe pneumonia (stage 3), and acute respiratory distress syndrome (stage 4). Among them, a low dose of LPS (2 mg/kg) may induce a pathological condition similar to pneumonia; medium dose of LPS (4 mg/kg) may induce a pathological condition similar to severe pneumonia; high dose of LPS (8 mg/kg) may induce a pathological condition similar to acute respiratory distress syndrome. Accordingly, we can use low-dose LPS to induce lung injury mimicking the early stage of pulmonary damage phase (phase II) in the novel coronavirus pneumonia, medium-dose LPS to induce lung injury mimicking the later stage of pulmonary damage phase (phase II) in the novel coronavirus pneumonia, and high-dose LPS to induce lung injury mimicking the cytokine storm phase (phase III) in the novel coronavirus pneumonia, thereby mimicking different progressions/illness severity in the novel coronavirus pneumonia.

Experimental Method 1

The acute lung injury animal model was developed by intratracheal administration of lipopolysaccharides (LPS) to 7~9 weeks-old SD rats. The rats have been treated with above-mentioned formula (or composition) before and after the injury in order to evaluate whether the occurrence of death or near-death as well as inflammation in rats are reduced, and to investigate whether the pharmaceutical composition of the present invention could reduce lung injury and inflammatory responses based on lung histopathology. The experimental design of this experiment is shown in Table 1.

TABLE 1

| Observation time | Groups | Replicates | Treatment methods | Experiment serial number |
|---|---|---|---|---|
| One day | Mock group | 5♂ | (1) Saline was given | 1, 2, 3, 4, 5 |
| | Control group (LPS) | 5♂ | (1) High dose LPS (8 mg/kg) was given at 0 min<br>(2) Saline was given 4 hours later<br>(3) Saline was given 8 hours later | 6, 7, 8, 9, 10 |
| | Experimental group A (high dose) | 5♂ | (1) The pharmaceutical composition for improving respiratory damage of the present invention (prepared as described above) was administered 30 mins earlier<br>(2) High dose LPS (8 mg/kg) was given at 0 min<br>(3) The pharmaceutical composition for improving respiratory damage of the present invention was administered 4 hours later<br>(4) The pharmaceutical composition for improving respiratory damage of the present invention was administered 8 hours later | 16, 17, 18, 19, 20 |

TABLE 1-continued

| Observation time | Groups | Replicates | Treatment methods | Experiment serial number |
|---|---|---|---|---|
| | Experimental group B (medium dose) | 4♂ | (1) The pharmaceutical composition for improving respiratory damage of the present invention was administered 30 mins earlier (2) Medium dose LPS (4 mg/kg) was given at 0 min (3) The pharmaceutical composition for improving respiratory damage of the present invention was administered 4 hours later (4) The pharmaceutical composition for improving respiratory damage of the present invention was administered 8 hours later | 2-2, 2-4, 2-5, 2-6 |
| | Experimental group C (low dose) | 4♂ | (1) The pharmaceutical composition for improving respiratory damage of the present invention was administered 30 mins earlier (2) Low dose LPS (2 mg/kg) was given at 0 min (3) The pharmaceutical composition for improving respiratory damage of the present invention was administered 4 hours later (4) The pharmaceutical composition for improving respiratory damage of the present invention was administered 8 hours later | 2-1, 2-7, 2-8, 2-9 |

Experiment Results

1. Mortality Rate

After treatment mortality rate is shown in Table 2. While the high-concentration LPS-induced acute lung injury group (Experimental group A) displays moderate mortality rate, in both of medium- and low-concentration LPS-induced acute lung injury groups (Experimental group B and Experimental group C), the mortality rate has been successfully reduced.

TABLE 2

| Groups | Replicates | Death Number | Mortality rate |
|---|---|---|---|
| Mock group | 5♂ | 0 | 0% |
| Control group | 5♂ | 2 | 40% |
| High dose experimental group A | 5♂ | 2 | 40% |
| Medium dose experimental group B | 4♂ | 0 | 0% |
| Low dose experimental group C | 4♂ | 0 | 0% |

2. Tests Related to Lung Injury

Test A. Improvement of Protein Accumulation in Lungs

Figure 2:
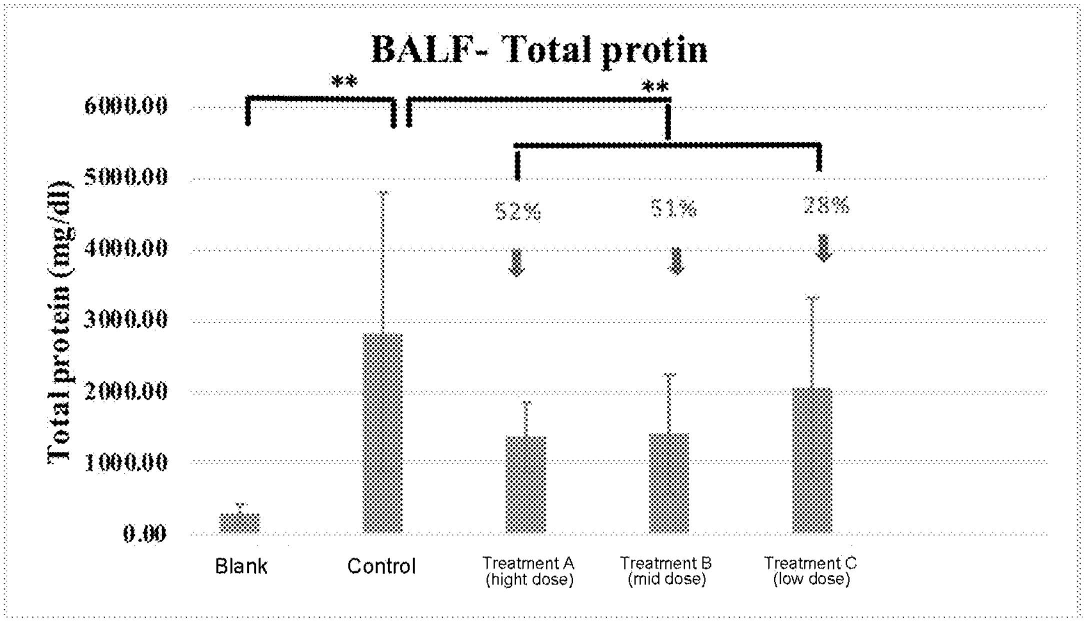
FIG. 2 illustrates bar graphs of the total protein contents in bronchoalveolar lavage fluid (BALF) for each treatment group.

The left lung lobe was irrigated with sterile PBS to collect bronchoalveolar lavage fluid (BALF). The total protein contents were detected using Enzyme-Linked Immunosorbent Assay (ELISA). The experimental results are referred in FIG. 2. The bar graphs show the total protein contents of bronchoalveolar lavage fluid (BALF) of each treatment group. As illustrated in FIG. 2, upon administration the pharmaceutical composition of the present invention significantly reduced the total protein contents of BALF in Experimental group A (high dose), Experimental group B (medium dose), and Experimental group C (low dose) by reducing 52%, 51%, and 28%, respectively. Apparently, the pharmaceutical composition of the present invention has efficacy to improve lung protein accumulation at each stage of the lung injury.

Test B. Improvement of Lung Inflammation

Figure 3:
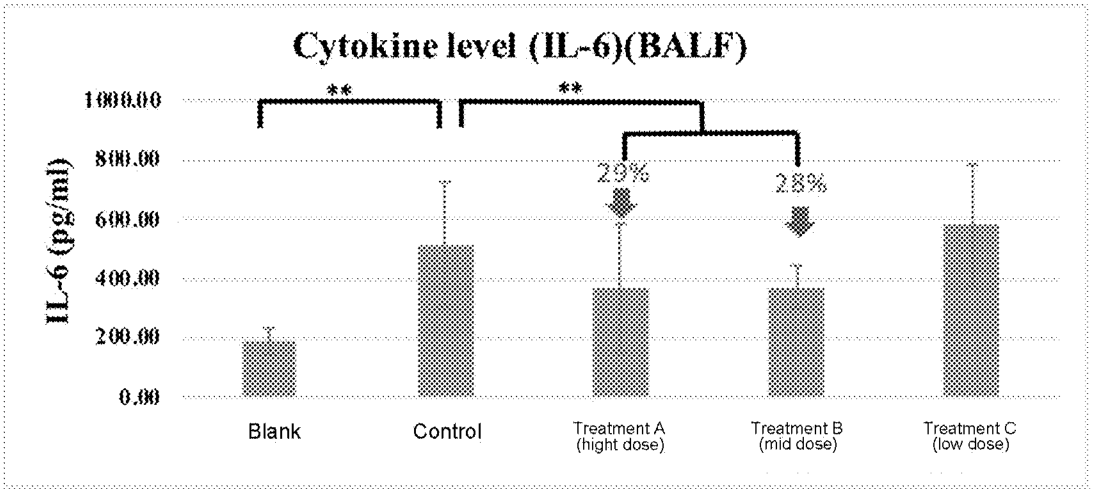
FIG. 3 and FIG. 4 are the schematic diagrams of bar graphs displaying IL-6 (FIG. 3) and IL-8 (FIG. 4) in bronchoalveolar lavage fluid (BALF) for each treatment group.
Figure 4:
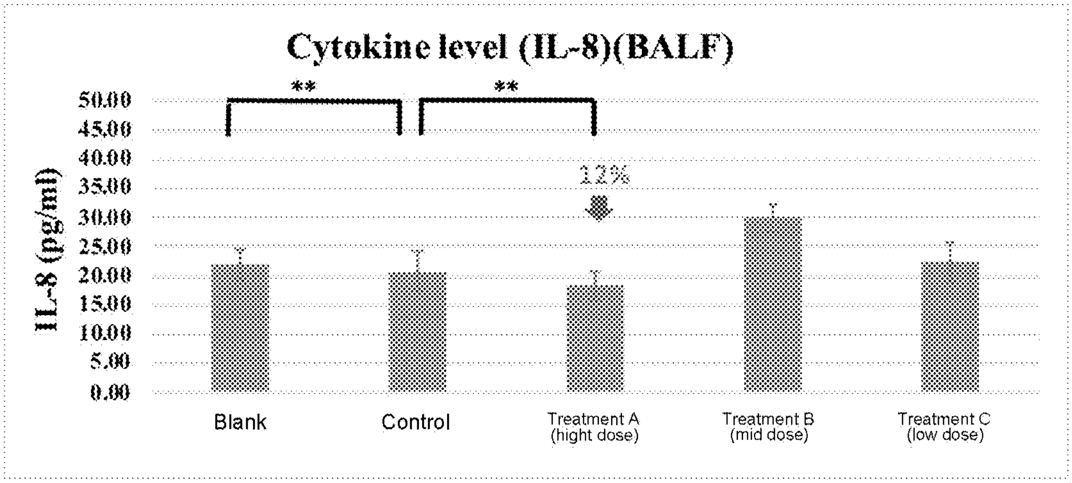

The left lung lobe was irrigated with sterile PBS to collect BALF. ELISA was used to quantify the concentrations of inflammatory factors including IL-6 and IL-8. Referring to FIG. 3 and FIG. 4, the schematic diagrams of bar graphs show IL-6 (FIG. 3) and IL-8 (FIG. 4) in the bronchoalveolar lavage fluid (BALF) for each treatment group. As shown in FIG. 3, in Experimental group A (high dose) and Experimental group B (medium dose), the pharmaceutical composition of the present invention, upon administration, significantly reduced the concentrations of inflammatory factor IL-6. As shown in FIG. 4, in Experimental group A (high dose), the concentration of IL-8 is significantly reduced. Apparently, the pharmaceutical composition of the present invention has efficacy to reduce inflammatory responses in lungs.

Test C. Improvements of Pulmonary Infiltrate and Pulmonary Edema

The remaining lung lobes (including right skull, right caudate lobe, and accessory lobe) were weighted, perfused with 0.8-1.0 mL of 10% of neutral buffered formalin (NBF), and then stored in 10 times volume of 10% NBF at room temperature for 72-96 hours. After fixation the lung lobes were trimmed and embedded in paraffin wax, then sectioned into 4-6 μm sections by a microtome. These sections were then stained evenly by hematoxylin and eosin (H&E).

Area of interest (AOI) from the lung lobe sections was magnified to 400× to determine the grades of polymorphonuclear cell infiltration (PMNL infiltration) and intra alveolar edema. Each field must include ≥95% alveoli, and evaluate ten random times to exam and quantify the pulmonary infiltrate and the intra alveolar edema. Standard grading system is shown in Table 3.

TABLE 3

| Grade | Description | Polymorphonuclear cell infiltration | Intra alveolar edema |
|---|---|---|---|
| 0 | None | 0 cell (400X view field) | 0% |
| 1 | Minimal | 1~5 cells (400X view field) | <25% |
| 2 | Minor | 6~10 cells (400X view field) | 26~50% |
| 3 | Moderate | Moderately infiltrated | 51~75% |
| 4 | Severe | Almost completely infiltrated | 76~100% |

Figure 5:
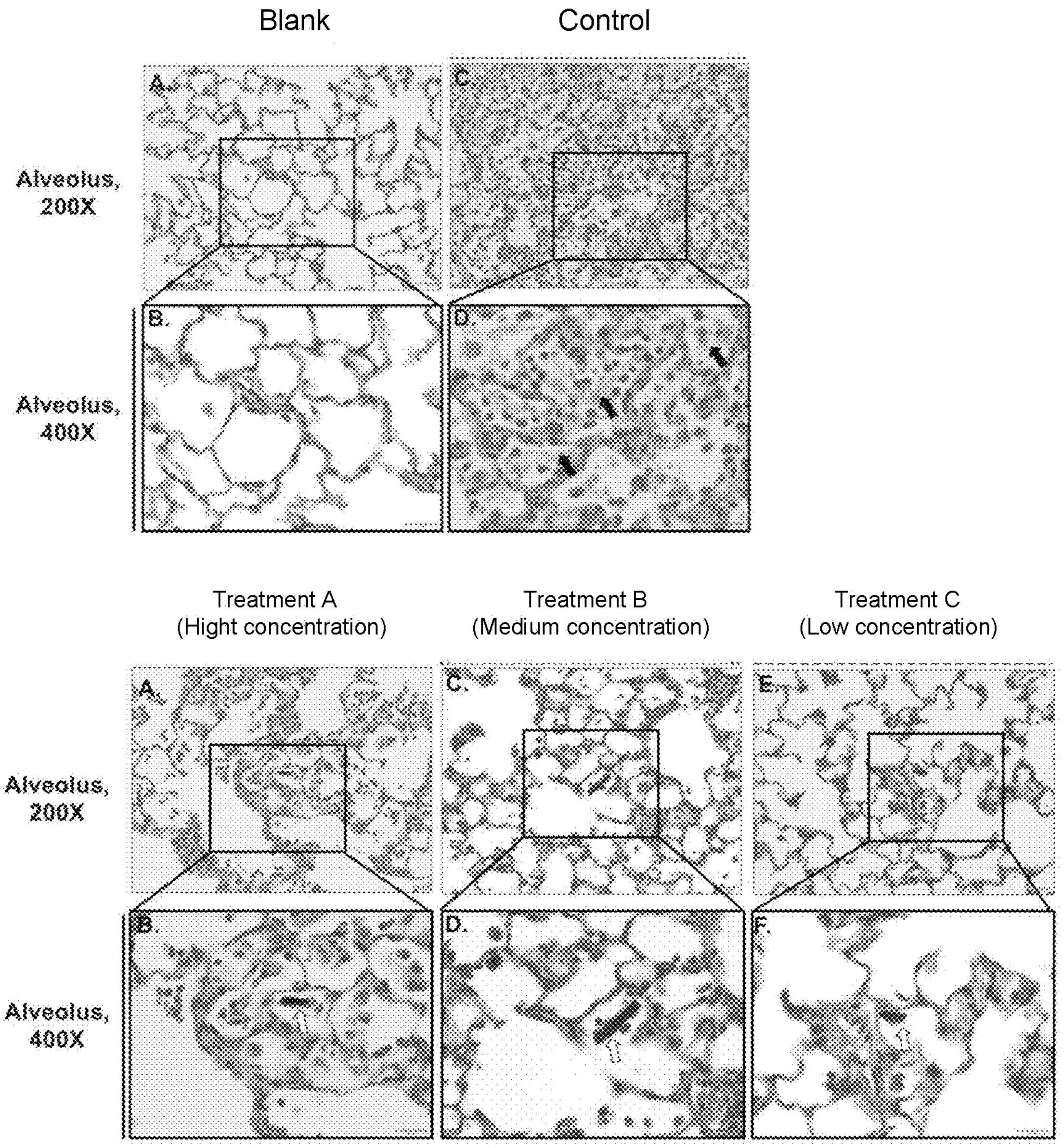
FIG. 5 illustrates H&E alveoli staining for each treatment group.
Figure 6:
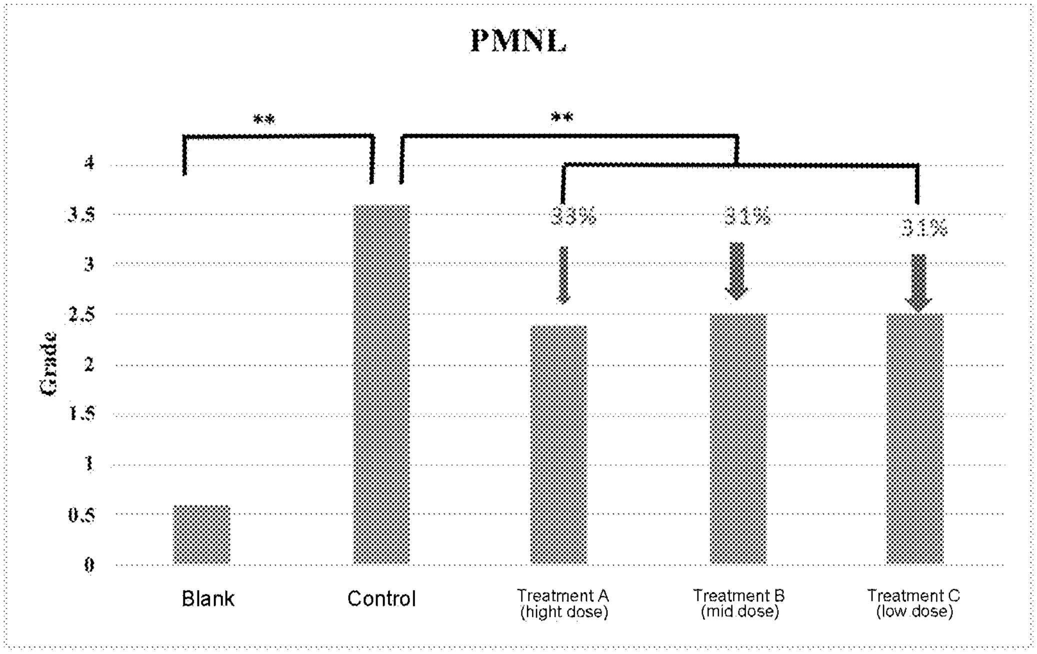
FIG. 6 illustrates quantitative graphs of polymorphonuclear cell infiltration measured according to the staining of FIG. 5.
Figure 7:
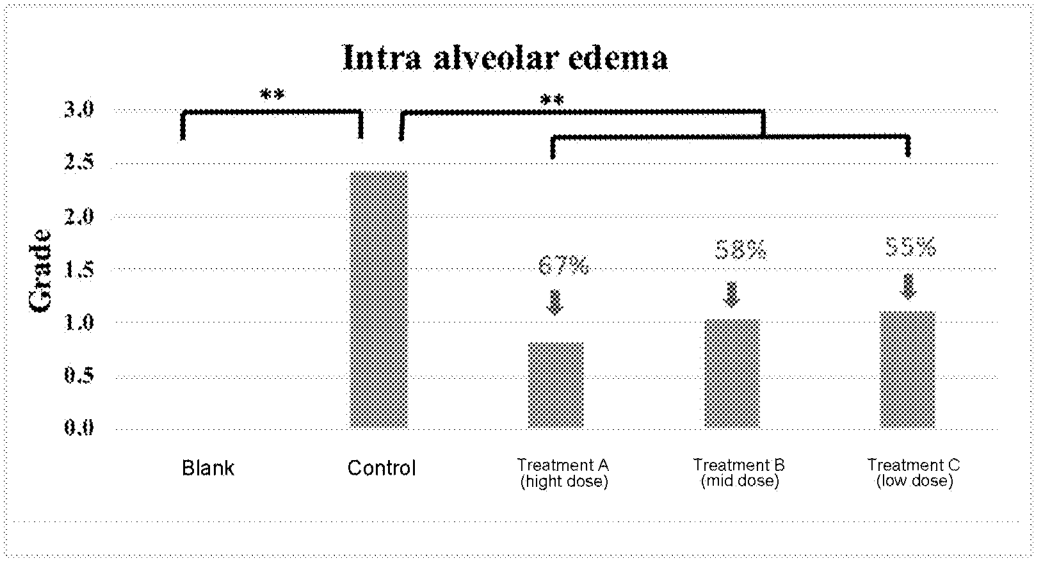
FIG. 7 illustrates quantitative graphs of intra alveolar edema measured according to the staining of FIG. 5.

Referring to FIG. 5, H&E alveoli staining for each treatment group is shown. FIG. 6 is the quantitative graph of polymorphonuclear cell infiltration measured according to the staining of FIG. 5. FIG. 7 is the quantitative graph of intra alveolar edema measured according to the staining of FIG. 5. As shown in FIGS. 5, 6 and 7, in all Experimental groups A, B, and C (high, medium, and low dose, respectively) upon administration the pharmaceutical composition of the present invention significantly reduced polymorphonuclear cell infiltration and intra alveolar edema. Apparently, the pharmaceutical composition of the present invention has efficacy to improve pulmonary infiltrate as well as intra alveolar edema.

Test D. Quantitative Graph of Lung Wet Weight

Figure 8:
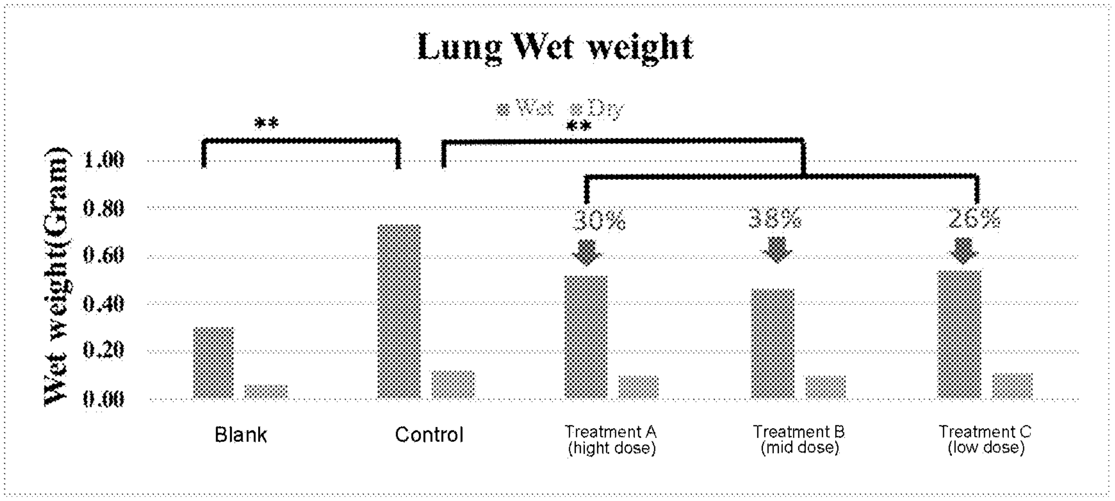
FIG. 8 illustrates quantitative graphs of lung wet weight for each treatment group.

To obtain the wet weight, the right middle lung lobe was cut and weighed by a calibrated scale. The sample was then placed in a 60° C. oven for 24 hours. Dry weight was taken using the same calibration scale. Referring to FIG. 8, a quantitative graph of lung wet weight for each treatment group is shown. As shown in FIG. 8, in Experimental group A, B, and C (high, medium, and low dose, respectively) upon administration the pharmaceutical composition of the present invention significantly reduced lung wet weight. Apparently, the pharmaceutical composition of the present invention significantly reduces the water contents in lung tissues and has efficacy to improve intra alveolar edema.

Figure 9:
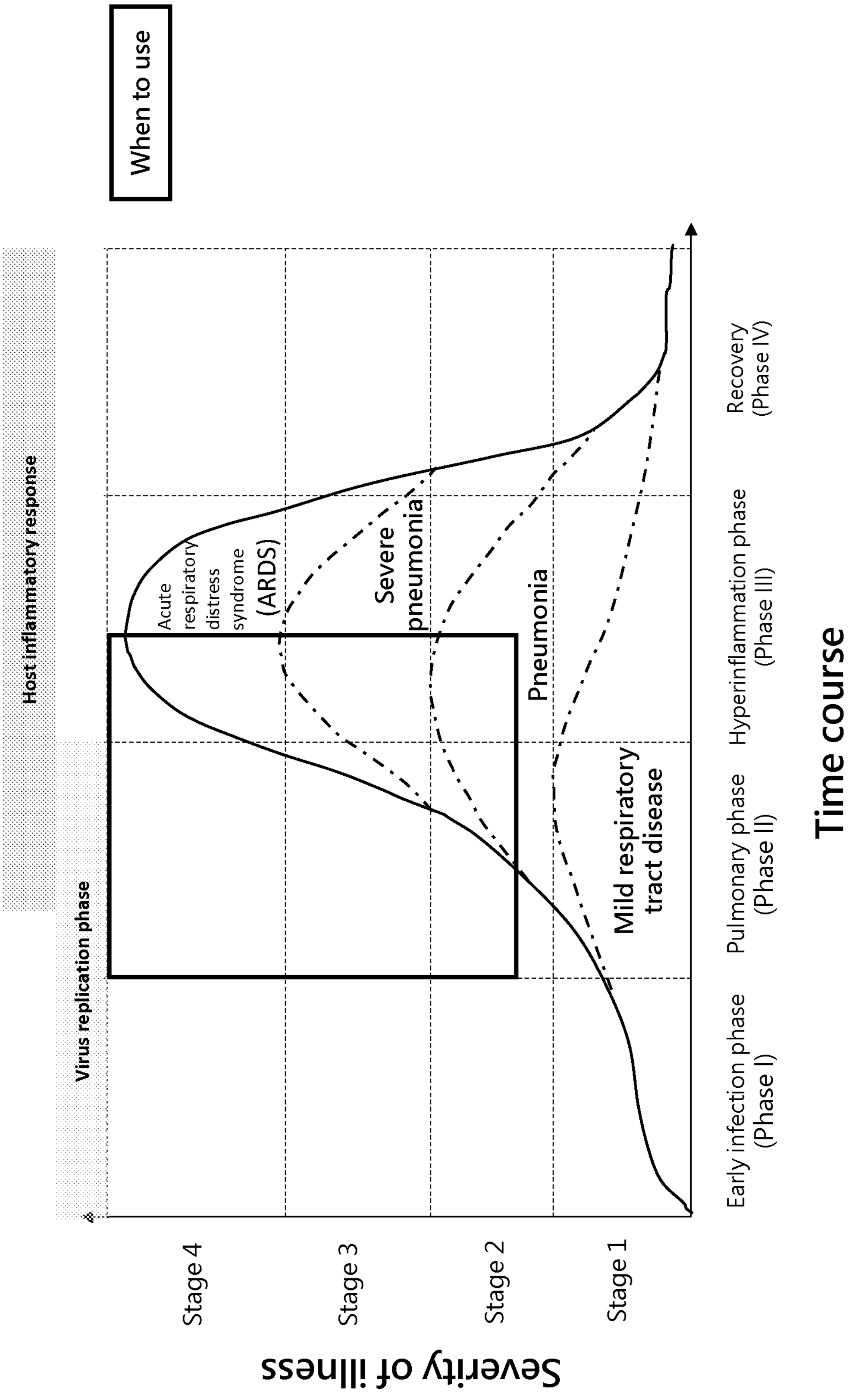
FIG. 9 is a schematic diagram of preferred timings to administer the pharmaceutical composition of the present invention.

Based on the above-mentioned experiments, it is understood that the pharmaceutical composition of the present invention indeed effectively improves various adverse symptoms in lungs and different progressions of the new coronavirus pneumonia. Referring to FIG. 9, a schematic diagram shows the preferred timings to administer the pharmaceutical composition of the present invention. As illustrated in FIG. 9, along with the previous experiments, the preferred clinical timings to administer the pharmaceutical composition of the present invention would be: (1) blood oxygen saturation ≤94% on room air, non-ventilated; (2) radiological evidence shows pulmonary infiltrate.

Experimental Method 2

The acute lung injury animal model was developed by intratracheal administration of lipopolysaccharides (LPS) to 7~9 weeks-old SD rats. The rats have been treated with above-mentioned formula (or composition) before or after the injury to assess whether the pharmaceutical composition of the present invention could reduce lung injury, inflammatory and alleviate lung fibrosis responses based on lung histopathology. The experimental design of this experiment is shown in Table 4.

TABLE 4

| Observation time | Groups | Replicates | Treatment methods | Experiment serial number |
|---|---|---|---|---|
| One day | Mock group | 5♂ | (1) Saline was given | 1, 2, 3, 4, 5, |
| | Control group (LPS) | 5♂ | (1) LPS (4 mg/kg) was given at 0 min<br>(2) Saline was given 4 hours later<br>(3) Saline was given 8 hours later | 3012, 3013, 3014, 3015, 3016 |
| | Treatment group | 10 ♀ | (1) LPS (4 mg/kg) was given at 0 min<br>(2) The pharmaceutical composition for improving respiratory damage of the present invention was administered 0.5 hours later<br>(3) The pharmaceutical composition for improving respiratory damage of the present invention was administered 2 hours later | 3022, 3023, 3024, 3025, 3026, 4010, 4011, 4012, 4013, 4014 |
| | Prevention group | 5♂ | (1) The pharmaceutical composition for improving respiratory damage of the present invention was administered 30 mins earlier<br>(2) LPS (4 mg/kg) was given at 0 min | 3043, 3044, 3045, 3046, 3047 |

Experiment Results

Figure 10:
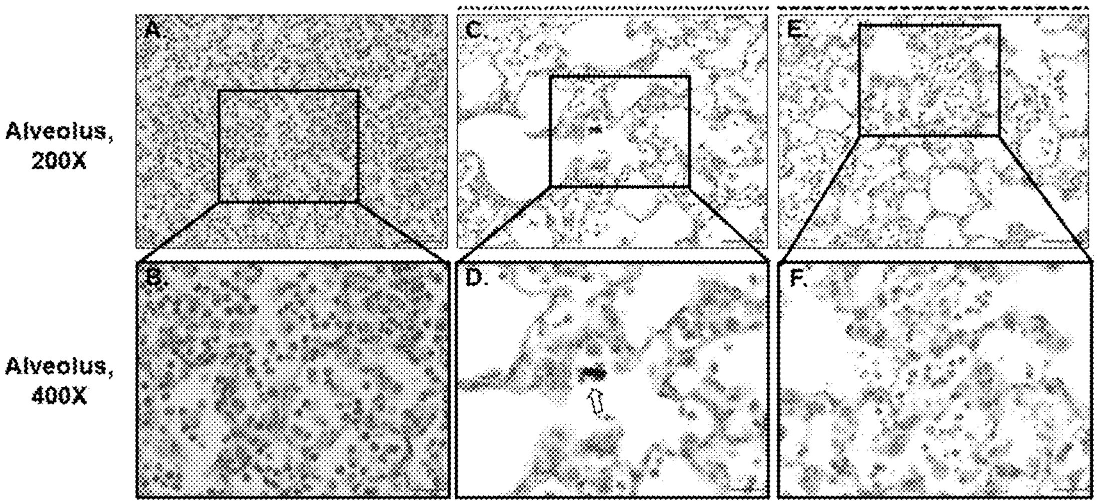
FIG. 10 illustrates H&E alveoli staining for each treatment group.

In FIG. 10, the alveolar H&E staining images for the Control group, Treatment group, and Prevention group of Experimental Method 2 are presented. Please refer to FIG. 5 for the alveolar H&E staining images of the Mock group. In the Control group, there is an observation of moderate to severe polymorphonuclear leukocyte (PMNL) infiltration and slight edema. Conversely, both the Treatment and Prevention groups exhibit mild to moderate PMNL infiltration. It has been found that the use of the pharmaceutical composition of the present invention can effectively reduce polymorphonuclear cell (PMNL) infiltration and intra-alveolar edema, with an improvement of approximately 50%. This indicates that whether administered before or after injury, the pharmaceutical composition of the present invention demonstrates efficacy in ameliorating pulmonary infiltration and edema. Furthermore, in comparison to the experimental study using nucleic acid enzyme inhibitor (Nin(+)) as a simulation of lung injury in COVID-19, excessive proliferation and deposition of lung fibrous tissues were observed. However, the Treatment group and Prevention group did not exhibit excessive proliferation and deposition of lung fibrous tissues, indicating that the pharmaceutical composition of the present invention has the efficacy to improve pulmonary fibrosis conditions.

In summary, the pharmaceutical composition provided by the present invention shows positive efficacy against pneumonia, regardless of its progression, and can achieve the effect of improving respiratory system damage, especially in terms of treating, alleviating, relieving, or preventing damage to the respiratory system. The respiratory system damage comprises inflammation, infection, pneumonia, and pulmonary fibrosis, either individually or in combination, within the respiratory system. The respiratory system damage encompasses a variety of upper respiratory tract infections affecting the nose, throat, larynx, and ear, specifically including Acute Sinusitis, Acute Laryngitis, Acute Tonsillitis, Acute Epiglottitis, Cribriform Inflammation, middle ear infections, and nasal allergies. Additionally, this damage extends to influenza and pneumonia, including viral pneumonia and bacterial pneumonia. Furthermore, lower respiratory tract conditions involve individual entities such as Acute Bronchitis, Acute Bronchiolitis, Chronic Bronchitis, Emphysema, Asthma, other Chronic Obstructive Pulmonary Diseases (COPD), Lung and mediastinal abscesses, Empyema, Bronchiectasis, and Bronchiectasis. Moreover, there are other respiratory ailments such as Acute Respiratory Distress Syndrome (ARDS), Farmer's Lung, Legionnaire's Disease, *Mycobacterium Avium*'s Disease, *Mycoplasma* Pneumonia, Pulmonary Fibrosis, Chronic Obstructive Pulmonary Diseases (COPD), Pulmonary Edema, Lung Injury, Emphysema, Lung Abscess, Extrinsic Allergic Alveolitis, Hypersensitivity Pneumonitis, Aspiration Pneumonia, Hemorrhagic Pneumonia, Tuberculosis Pneumonia, and Extrinsic Pneumonia.

What is claimed is:

1. A pharmaceutical composition for improving respiratory damage, comprising an adsorbent medicament, wherein said adsorbent medicament comprises a carbon material and a water-containing carrier, wherein said carbon material is selected from a group consisting of activated carbon, activated carbon fiber, activated carbon ball, columnar activated carbon, activated carbon powder, and a combination thereof, wherein said carbon material has a mean particle diameter ranging from 0.1 to 500 μm, wherein said carbon material has a specific surface area (BET) ranging from 300 to 3000 m2/g, wherein said carbon material has a micropore diameter ranging from 1 to 500 nm, wherein said water-containing carrier is selected from the group consisting of normal saline, buffers, isotonic saline solution, and a combination thereof, said adsorbent medicament mixed with said water-containing carrier is formulated as a suspension at a concentration ranging from 0.001 to 1 wt %, wherein the adsorbent carbon material is configured for administration into a respiratory system by inhalation or instillation to be delivered to a respiratory tract, lungs, or alveoli, to adsorb toxic substances, bacteria, viruses, proinflammatory cytokines, chemokines, or cytokines in the respiratory system, and wherein the pharmaceutical composition improves respiratory system damage.

2. The pharmaceutical composition according to claim 1, wherein said carbon material has a volume in pores ranging from 0.1 to 3.0 ml/g.

3. The pharmaceutical composition according to claim 1, wherein said pharmaceutical composition further comprises at least one of an adjuvant, an excipient, or a propellant.

4. The pharmaceutical composition according to claim 1, further comprising a medicine selected from a group consisting of an antibacterial medicine, an antiviral medicine, an anticoagulant medicine, a thrombolytic medicine, an alpha-blocker, a 5a-Reductase inhibitor, a nasal decongestant, an antitussive, an expectorant, a mucolytic, a bronchodilator, an antibiotic, an antifungal medicine, an antiasthmatic medicine, an anti-inflammatory medicine, an antioxidant, a Chinese medicine extract, an antibody, and a vaccine.

5. The pharmaceutical composition according to claim 1, wherein said carbon material further comprises at least one of oxygen functional groups, hydroxyl functional groups, hydroxyl, carboxylic acid, aldehyde groups, and carbonic acid.

6. The pharmaceutical composition according to claim 1, further comprising an element selected from a group consisting of metal ions, magnetic materials, cation compounds, anion compounds, or halogen ions, and a combination thereof.

7. A method for improving respiratory damage, the method comprising:

(a) providing a pharmaceutical composition comprising an adsorbent medicament, wherein said adsorbent medicament comprises a carbon material and a water-containing carrier;

(b) administering said pharmaceutical composition into a respiratory system of the patient by inhalation or instillation to deliver the carbon material to a respiratory tract, lungs, or alveoli, to adsorb toxic substances, bacteria, viruses, proinflammatory cytokines, chemokines, or cytokines in the respiratory system; and (c) removing the pharmaceutical composition out of the lungs of the patient, wherein said carbon material is selected from the group consisting of activated carbon, activated carbon fiber, activated carbon ball, columnar activated carbon, activated carbon powder, and a combination thereof, wherein said carbon material has a mean particle diameter ranging from 0.1 to 500 μm, a specific surface area (BET) ranging from 300 to 3000 $m^2/g$, and a micropore diameter ranging from 1 to 500 nm, wherein said water-containing carrier is selected from the group consisting of normal saline, buffers, isotonic saline solution, and a combination thereof, and wherein said adsorbent medicament mixed with said water-containing carrier is formulated as a suspension at a concentration ranging from 0.001 to 1 wt %.

* * * * *